United States Patent
Hsia et al.

(10) Patent No.: US 10,583,098 B2
(45) Date of Patent: Mar. 10, 2020

(54) TOPICAL CO-ENZYME Q10 FORMULATIONS AND TREATMENT OF PAIN, FATIGUE AND WOUNDS

(76) Inventors: Sung Lan Hsia, Miami, FL (US);
Niven Rajin Narain, Miami, FL (US);
Indushekhar Persaud, Homestead, FL (US)

( * ) Notice: Subject to any disclaimer, the term of this patent is extended or adjusted under 35 U.S.C. 154(b) by 911 days.

(21) Appl. No.: 12/299,354

(22) PCT Filed: May 2, 2007

(86) PCT No.: PCT/US2007/068052
§ 371 (c)(1),
(2), (4) Date: Sep. 3, 2009

(87) PCT Pub. No.: WO2007/131047
PCT Pub. Date: Nov. 15, 2007

(65) Prior Publication Data
US 2010/0062048 A1    Mar. 11, 2010

Related U.S. Application Data

(60) Provisional application No. 60/797,008, filed on May 2, 2006.

(51) Int. Cl.
| | | |
|---|---|---|
| A61K 9/127 | (2006.01) |
| A61K 31/122 | (2006.01) |
| A61K 9/00 | (2006.01) |
| A61K 9/12 | (2006.01) |
| A61K 9/10 | (2006.01) |

(52) U.S. Cl.
CPC .......... *A61K 31/122* (2013.01); *A61K 9/0014* (2013.01); *A61K 9/10* (2013.01); *A61K 9/122* (2013.01); *A61K 9/127* (2013.01)

(58) Field of Classification Search
USPC .......................................... 424/450
See application file for complete search history.

(56) References Cited

U.S. PATENT DOCUMENTS

| | | | |
|---|---|---|---|
| 4,636,381 A | | 1/1987 | Takada et al. |
| 4,895,727 A | | 1/1990 | Allen |
| 5,863,556 A | * | 1/1999 | Ruckert et al. ............... 424/450 |
| 5,891,469 A | | 4/1999 | Amselem |
| 5,989,583 A | | 11/1999 | Amselem |
| 6,048,846 A | | 4/2000 | Cochran |

(Continued)

FOREIGN PATENT DOCUMENTS

| | | |
|---|---|---|
| DE | 19905879 A1 | 8/2000 |
| EP | 0069399 * | 7/1982 |

(Continued)

OTHER PUBLICATIONS

International Search Report from International Application No. PCT/US2007/068052 dated Apr. 15, 2008.

(Continued)

*Primary Examiner* — Gollamudi S Kishore
(74) *Attorney, Agent, or Firm* — McCarter & English, LLP; Jill Mello

(57) ABSTRACT

CoQ10 has a stimulatory effect on fibroblasts and keratinocytes, increases ATP production, decreases pain. The formulations are useful for promoting acute wound healing, fatigue and treatment of acute and chronic pain.

31 Claims, 13 Drawing Sheets

(56) References Cited

U.S. PATENT DOCUMENTS

| | | | |
|---|---|---|---|
| 6,312,720 B1 * | 11/2001 | Katinger et al. | 424/450 |
| 6,348,506 B2 | 2/2002 | Sneed | |
| 6,465,517 B1 | 10/2002 | Van Der Zee | |
| 6,569,463 B2 | 5/2003 | Patel et al. | |
| 6,726,924 B2 | 4/2004 | Keller | |
| 6,753,325 B2 | 6/2004 | Rosenbloom | |
| 6,764,693 B1 * | 7/2004 | Smith | 424/450 |
| 6,923,988 B2 | 8/2005 | Patel et al. | |
| 7,005,274 B1 | 2/2006 | Terkeltaub et al. | |
| 7,060,733 B2 | 6/2006 | Pandol et al. | |
| 7,273,606 B2 | 9/2007 | Fantuzzi et al. | |
| 2002/0034537 A1 * | 3/2002 | Schulze et al. | 424/450 |
| 2002/0039595 A1 * | 4/2002 | Keller | 424/450 |
| 2002/0048551 A1 * | 4/2002 | Keller et al. | 424/43 |
| 2002/0058712 A1 * | 5/2002 | Sneed | 514/678 |
| 2002/0136711 A1 | 9/2002 | Cochran | |
| 2002/0156062 A1 * | 10/2002 | Boch et al. | 514/185 |
| 2002/0198177 A1 | 12/2002 | Horrobin | |
| 2003/0103954 A1 | 6/2003 | Rosenbloom | |
| 2003/0105027 A1 | 6/2003 | Rosenbloom | |
| 2003/0105031 A1 | 6/2003 | Rosenbloom | |
| 2003/0118536 A1 | 6/2003 | Rosenbloom | |
| 2003/0232033 A1 * | 12/2003 | Cantrell | 424/85.5 |
| 2003/0236239 A1 * | 12/2003 | Brancato et al. | 514/183 |
| 2004/0034107 A1 * | 2/2004 | Enzmann | 514/690 |
| 2004/0037828 A1 * | 2/2004 | Tennenbaum et al. | 424/144.1 |
| 2004/0063661 A1 | 4/2004 | Linnane | |
| 2004/0115181 A1 | 6/2004 | Fujii et al. | |
| 2004/0247658 A1 * | 12/2004 | Trubiano et al. | 424/450 |
| 2005/0019268 A1 | 1/2005 | Enzmann | |
| 2005/0025756 A1 | 2/2005 | Erwin | |
| 2005/0070610 A1 | 3/2005 | Fujii et al. | |
| 2005/0084505 A1 * | 4/2005 | Muller et al. | 424/400 |
| 2005/0208118 A1 * | 9/2005 | Takemoto | 424/450 |
| 2005/0239721 A1 | 10/2005 | Rosenbloom | |
| 2006/0110415 A1 | 5/2006 | Gupta | |
| 2006/0251708 A1 * | 11/2006 | Chen et al. | 424/450 |
| 2007/0009583 A1 * | 1/2007 | Qvist | 424/445 |
| 2007/0026072 A1 | 2/2007 | Olsen et al. | |
| 2009/0098201 A1 * | 4/2009 | Smith | 424/457 |
| 2012/0231038 A1 * | 9/2012 | Trexler et al. | 424/400 |
| 2013/0323335 A1 * | 12/2013 | Rozenblat et al. | 424/741 |

FOREIGN PATENT DOCUMENTS

| | | |
|---|---|---|
| EP | 0261362 A3 | 5/1989 |
| EP | 1588703 A4 | 6/2008 |
| EP | 1281398 B1 | 7/2008 |
| JP | 62077318 * | 4/1987 |
| WO | WO 2005/069916 A1 | 8/2005 |
| WO | WO-2005/069916 A1 | 10/2006 |

OTHER PUBLICATIONS

Health Care Purchasing News, 2004, http://www.hpnonline.comlinside/2004-12/editors_board.htm.

Ogura et. al, Effect of CoQ10 Liposome Lotion on Lipid Peroxidation in the Epidermis Exposed to Ultraviolet Light, Journal of the Kurume Medical Association, 1986, 49, no. 1, pp. 64-69 (with English Abstract).

Johnson et al., Partial-Thickness Burns: Identification and Management, Advances in Skin & Wound Care, Clinical Management Extra,16(4):178-189, 2003.

Playford et al., Combined effect of coenzyme Q10 and fenofibrate on forearm microcirculatory function in type 2 diabetes. Atherosclerosis. May 2003;168(1):169-79.

* cited by examiner

A: WOUND EXCISION
B: PLACEMENT OF SPECIMEN IN SODIUM BROMIDE FOR INCUBATION
C: PLACEMENT OF SPECIMEN ON GLASS SLIDE FOR SEPARATION
D: SEPARATION OF SPECIMEN
E: PLACEMENT OF EPIDERMAL SPECIMEN ON CARDBOARD FOR PERMANENT RECORD

TOPICAL CO-ENZYME Q10 FORMULATIONS AND TREATMENT OF PAIN, FATIGUE AND WOUNDS

CROSS-REFERENCE TO RELATED APPLICATIONS

This application is a U.S. National Stage application claiming priority under 35 U.S.C. § 371 to International Application No. PCT/US2007/068052, filed on May 2, 2007 which, in turn, claims the benefit of and priority to U.S. Provisional Patent Application No. 60/797,008, filed May 2, 2006, the entire disclosures of each of which are incorporated by reference herein.

FIELD OF INVENTION

The invention provides pharmaceutical compositions comprising co-enzyme Q10 (CoQ10) and methods of using CoQ10 for treatment of pain, muscle fatigue, wound healing, arthritis and the like.

BACKGROUND

An area of on-going research is the development of safer and effective methods for reducing or eliminating pain using transdermal analgesic formulations. While many of the currently available analgesic formulations reduce pain to some degree, there is, nonetheless, a continued interest in identifying new formulations which provide longer lasting pain relief in a short period of time.

It is therefore an object of the present invention to provide a safe topical composition that provides effective pain relief in a sufficiently short period of time, and also treats fatigue, and accelerates wound healing. Further objects of the present invention will be apparent from the descriptions herein.

SUMMARY

The invention provides a composition comprising CoQ10 and phospholipid liposomes. The present invention is also directed to methods of treating pain, fatigue, wound-healing, and decreased ATP production.

In a preferred embodiment, a topical composition for the treatment of pain, fatigue and wound healing comprising CoQ10, liposomes and a pharmaceutically acceptable carrier. Preferably, the composition comprises between about 0.001% to about 60% (w/w) of Coenzyme Q10.

In another preferred embodiment, the composition is in the form of a gel, ointment, cream, salve, lotion, mousse, foam, spray and/or aerosol.

In another preferred embodiment, a method of treating pain associated with cancer comprises topically administering to a patient in need thereof, a topical composition comprising a therapeutically effective amount of a composition of CoQ10, liposomes and a pharmaceutically acceptable carrier to the area of pain. Preferably, the composition comprises between about 0.001% to about 60% (w/w) of Coenzyme Q10.

In another preferred embodiment, a method of treating pain associated with muscle pain comprises topically administering to a patient in need thereof, a topical composition comprising a therapeutically effective amount of the composition of CoQ10, liposomes and a pharmaceutically acceptable carrier to the area of pain. Preferably, the composition comprises between about 0.001% to about 60% (w/w) of Coenzyme Q10.

In another preferred embodiment, a method of treating pain associated with joint pain comprises topically administering to a patient in need thereof, a topical composition comprising a therapeutically effective amount of the composition of CoQ10, liposomes and a pharmaceutically acceptable carrier to the area of pain. Preferably, the composition comprises between about 0.001% to about 60% (w/w) of Coenzyme Q10.

In another preferred embodiment, a method of treating pain, fatigue and wound healing comprises topically administering to a patient in need thereof, a topical composition comprising a therapeutically effective amount of the composition of CoQ10, liposomes and a pharmaceutically acceptable carrier to the area of pain. Preferably, the composition comprises between about 0.001% to about 60% (w/w) of Coenzyme Q10. Pain can be the result of any affliction, such as for example, physical injury, cuts, burns, surgery, joint, muscle, head, neck, cancer, disease, age-related and the like.

In another preferred embodiment, a method of treating muscle fatigue comprises topically administering to a patient in need thereof, a topical composition comprising a therapeutically effective amount of the composition of CoQ10, liposomes and a pharmaceutically acceptable carrier to the to the muscle. Preferably, the composition comprises between about 0.001% to about 60% (w/w) of Coenzyme Q10.

In another preferred embodiment, a method of increasing ATP production in muscles, comprises administering to a patient in need thereof, a topical composition comprising a therapeutically effective amount of a composition comprising coenzyme Q10, liposomes in a pharmaceutically acceptable carrier to the muscles. However, the increase in ATP production can be in any cell.

In another preferred embodiment, a method of accelerating wound healing comprises administering to a patient in need thereof, a topical composition comprising a therapeutically effective amount of coenzyme Q10, liposomes in a pharmaceutically acceptable carrier to the muscles.

In another preferred embodiment, a composition for the treatment of pain and wound healing comprises CoQ10, liposomes, and a pharmaceutically acceptable carrier. Preferably, the composition comprises between about 0.001% to about 60% (w/w) of Coenzyme Q10.

In another preferred embodiment, the composition further comprises cytokines, growth factors, differentiation factors, hormones, analgesics and pain-killers. Examples of cytokines are growth factors, migratory factors, monokines, lymphokines and include, but not limited to: Epidermal Growth Factor (EGF); Platelet-Derived Growth Factor (PDGF); Fibroblast Growth Factors (FGFs); Transforming Growth Factors-$\beta$ (TGFs-$\beta$); Transforming Growth Factor-$\alpha$ (TGF-$\alpha$); Erythropoietin (Epo); Insulin-Like Growth Factor-I (IGF-I); Insulin-Like Growth Factor-II (IGF-II); Interleukin-1 (IL-1); Interleukin-2 (IL-2); Interleukin-6 (IL-6); Interleukin-8 (IL-8); Tumor Necrosis Factor-$\alpha$ (TNF-$\alpha$); Tumor Necrosis Factor-$\beta$ (TNF-$\beta$); Interferon-$\gamma$ (INF-$\gamma$); Colony Stimulating Factors (CSFs) and the like.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
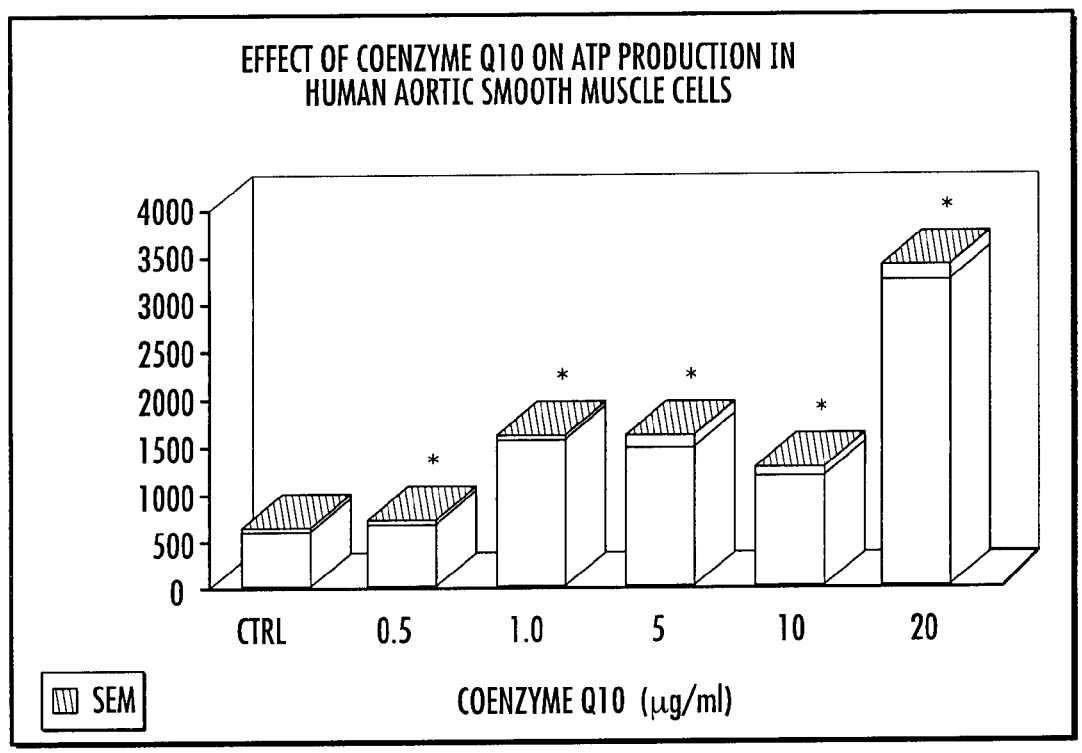
FIG. 1 is a graph showing the effect of coenzyme Q10 on ATP production in human aortic smooth muscle cells. *Significant compared to Ctrl, P<0.05, One-way ANOVA and Dunnett's.

The invention provides a composition comprising CoQ10 and phospholipid liposomes. The present invention is also directed to methods of treating pain, fatigue, wound-healing, and decreased ATP production.

Definitions

In accordance with the present invention and as used herein, the following terms are defined with the following meanings, unless explicitly stated otherwise.

As used herein, "a", "an," and "the" include plural references unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, accelerate wound healing, relief of pain and fatigue. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, "an ameliorated symptom" or "treated symptom" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

The term "athlete" refers to an individual who participates in sports at any level and who seeks to ameliorate muscle fatigue, pain, wound healing and the like. However, those athletes who are bicyclists, long distance runners, short distance runners will also benefit from the effects of the present invention. An athlete may be hard training, that is, performs sports activities intensely more than three days a week or for competition. An athlete may also be a fitness enthusiast who works out for about 1-2 hours about 1-3 times a week.

The term "wound healing" and "improved wound healing" refers to the healing of wounds using the compositions of the invention. The term encompasses not only accelerated wound healing, i.e. as compared to 1) a control wherein the patient is not treated and 2) treatment with known wound healing medicaments. The term also encompasses other parameters related to improved quality and quantity of healing. This wound include, but not limited to faster healing, stronger healing, less pain, reduced scar tissue, improved cosmetic outcome and promotion of other processes associated with wound healing.

Subjects

Subjects from many different species can be treated with the compositions of the invention. A non-exhaustive exemplary list of such animals includes mammals such as mice, rats, rabbits, goats, sheep, pigs, horses, cattle, dogs, cats, and primates such as monkeys, apes, and human beings. Those animal subjects known to suffer muscle fatigue, pain, wounds are preferred for use in the invention. In particular, human patients suffering from injuries, surgery, arthritis, muscle fatigue and the like are suitable animal subjects for use in the invention. By adapting the methods taught herein to other methods known in medicine or veterinary science (e.g., adjusting doses of administered substances according to the weight of the subject animal), the compositions utilized in the invention can be readily optimized for use in other animals.

Pharmaceutical Compositions and Administration to a Subject

In a preferred embodiment, the invention provides CoQ10 compositions for the treatment of wounds, pain, fatigue and the like. Transdermal, oral and intravenous preparations of 2,3-dimethoxy-5-methyl-6-decaprenyl-1,4-benzoquinone (coenzyme Q-10) comprise, inter alia, auxiliary agents, an effective amount of pulmonary surfactant, and/or in combination with liposomes.

In a preferred embodiment, the invention provides CoQ10 compositions for pain, fatigue and wound healing. Preferably, the compositions comprise at least about 0.001% to about 60% (w/w) of Coenzyme Q10.

To deliver a CoQ10-containing composition, any suitable carrier can be used. Liposomes, for example, may be used as a carrier. An exemplary liposomal formulation is composed of Phospholipon 90G (American Lechitin, Stanford, Conn.), Phospholipon 90H (American Lechitin, Stanford, Conn.), Glycerol, Butylated hydroxytoluene (BHT), Ethanol, Medium Chain Triglycerides (MCT), lavender (Sigma-Aldrich, St. Louis, Mo.) and Coenzyme Q10 (Pure Prescriptions, San Diego, Calif.). An example of a protocol for preparing this formulation entails first dissolving 10 g of Phospholipon 90H, 5 g Phospholipon 90G, with 1.5 g MCT, 0.3 g BHT, and 9 ml of ethanol at 75° C. Next, 1.1 g of Coenzyme Q10 are dissolved into the mixture. 65 ml of 1 mM phosphate buffer (pH 8.2) prepared with nitrogen saturated water, 13.3 g glycerol, and 50 µL of lavender are added. The above mixture is blended in a high-speed blender at 12,000 RPM to form a cream. The cream is stored at 4° C. until used.

In a preferred embodiment, the CoQ10 compositions can further comprises CoQ10, liposomes, and a pharmaceutically acceptable carrier. Preferably, the composition comprises between about 0.001% to about 60% (w/w) of Coenzyme Q10. For example, Q-soothe comprises 1% w/w of coenzyme Q10.

In another preferred embodiment, the composition further comprises cytokines, growth factors, differentiation factors, hormones, pain-killers and/or analgesics. Examples of cytokines are growth factors, migratory factors, monokines, lymphokines.

Examples of suitable growth factors are basic fibroblast growth factor (bFGF), vascular endothelial growth factor (VEGF), epidermal growth factor (EGF), transforming growth factors (TGFα and TGFβ), platelet derived growth factors (PDGFs), hepatocyte growth factor (HGF), insulin-like growth factor (IGF), insulin, erythropoietin (EPO), and colony stimulating factor (CSF). Examples of suitable hormone medium additives are estrogen, progesterone, testosterone or glucocorticoids such as dexamethasone. Examples of cytokines are interferons, interleukins, or tumor necrosis factor-α (TNFα).

Some examples of interleukins include IL-1, -2, -3, -4, -5, -6, -7, -8, -9, -10, -11, -12, -13, -14, -15, -16, -17, -18, -19, -20, and -21.

Examples of analgesics or anti-inflammatories to alleviate pain, include for example, NSAIDS and Cox-2-inhibitors. When used in such manner, for example, the composition herein can provide an enhanced and/or additive pain relief effect.

Other pain-killers that can be included in the composition are, for example, morphine-like agents, such as codeine, opiates, oxy-contin, Percocet, Demorol, and Vicadin. When used in such manner, for example, the morphine-like agents, together with any of the formulations of the present invention, can achieve an analgesic effect that would otherwise require a higher dosage of opioids but with fewer side effects.

In one preferred embodiment, the compositions comprising CoQ10 are administered topically. It is preferable to present the active ingredient, i.e. CoQ10 as a pharmaceutical formulation. Coenzyme Q10 is available commercially. Exemplary compositions are described in detail in the examples which follow. The active ingredient may comprise, for topical administration, from 0.001% to about 60% w/w, by weight of the formulation in the final product, although it may comprise as much as 80% w/w, preferably from about 0.001% to about 60% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

The composition of the invention can be administered to a patient either by themselves, or in pharmaceutical compositions where it is mixed with suitable carriers or excipient (s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

The compositions of the invention can be applied to a patient by treatment modalities that are tailored to the patient, such as the type of injury, severity of the injury, location of the injury. For example, the percentage of the active composition can be modulated during the course of treatment again depending on severity, type of injury etc. CoQ10 the active ingredient, may comprise, from 0.001% to about 60% w/w, by weight of the formulation in the final product, although it may comprise as much as 80% w/w, preferably from about 0.001% to about 60% w/w of the formulation.

The compositions can be applied to a patient at least once a day. In other embodiments the pharmaceutical compositions can be applied, twice a day, three times a day or more. The times and compositions containing the active ingredients can easily be determined by a clinician.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of cancer with topical formulations of CoQ10, in other aspects of the invention CoQ10 might be delivered by other methods. For example, CoQ10 might be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to ATP production in a cell or in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methyl-cellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. CoQ10 is facilitated. Without violating this constraint, the pH may be selected to improve CoQ10 compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of CoQ10. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like.

Also suitable as skin penetration enhancers are organic acids and esters such as salicyclic acid, methyl salicylate, citric acid, succinic acid, and the like.

Effective Amounts

The compositions described above are preferably administered to a subject in an effective amount. An effective amount is an amount which is capable of producing a desirable result in a treated animal or cell. As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for topical administration of the compositions of the invention would be in the range of about 0.1-2.50 mg CoQ10/kg of body weight (e.g., 10-500 mg for subjects ranging from 110 to 300 lbs. An effective amount for use with a cell in culture will also vary, but can be readily determined empirically (for example, by adding varying concentrations to the cell and selecting the concentration that best produces the desired result). It is expected that an appropriate concentration would be in the range of about 1-250 µM.

Conditions/Disorders

In a preferred embodiment, the compositions of the invention, i.e. comprising Coenzyme Q10 as the active ingredient are used to treat muscle and skeletal muscle fatigue, accelerate wound healing, provide improved wound healing, pain such as joint pain, general fatigue and the like. Without wishing to be bound by theory, it is thought that the compositions increase ATP in a cell.

ATP is a nucleotide molecule having three phosphate molecules attached to a 5-hydroxyl group on a ribose of adenosine, which has a formal name of adenosine 5'-triphosphate. ATP is a compound widely present in any living tissue or organism including animal's muscles or yeast cells.

ATP has two high-energy phosphate bonds per molecule, thereby yielding a free energy of about 7.3 kcal/mol when hydrolyzed around a neutral pH and itself being converted into adenosine diphosphate. Thus, the energy yielded from ATP hydrolysis allows nucleic acid synthesis as well as various metabolisms including protein metabolism, carbohydrate metabolism and/or lipid metabolism. A compound having a phosphate ester bond provided from ATP will enter an "activated state" to contribute to various synthesis reactions.

ATP is the essential energy production molecule for every cell in the body. Similar phosphate-rich compounds are also found in every organism with ATP related compounds supplying all cellular energy. In 1982, Chaudry at the Yale Medical School published results showing that ATP was present in intracellular and interstitial fluids, thereby suggesting ATP's greatly expanded biological importance.

ATP and its breakdown product adenosine are also inherently involved in a number of extracellular processes like that of muscle contraction as described above. For example, some of these extracellular processes include neurotransmission, cardiac function, platelet function, vasodilatation and liver glycogen metabolism. As can be appreciated, these additional biological roles have given rise to various clinical applications of ATP and adenosine. For example, clinical applications may include applications of ATP and adenosine as a neuropathic and ischemic anesthetic, a hypotensive agent for trauma or disease induced hypertension such as pulmonary hypertension, a mild hypoglycemic in type II diabetes and at least preliminary evidence that ATP may be useful as an adjunctive therapy for radiation cancer treatment.

ATP and related compounds have been researched extensively for possible drug uses (see Daly, *J. Med. Chem.*, 25:197, (1982)). The most widespread of these applications is in various cardiac treatments including the prevention of reperfusion injury after cardiac ischemia or stroke, and treatment of hypertension (see Jacobson, et al., *J. Med. Chem.*, 35, 407-422 (1992)) as well as the treatment of paroxysmal supra ventricular tachycardia (see Pantely, et al., *Circulation*, 82, 1854 (1990)).

With regards to human performance specifically, the splitting of ATP to form adenosine diphosphate (ADP) is of critical importance in the functioning of muscle, since this is the reaction that directly supplies energy to myosin and actin to facilitate normal muscular contraction. In many cases, this requirement is met by the actual rebuilding of ATP as it is used, rather than by storing a very large amount of ATP in the muscle. However, under exceptionally demanding conditions such as peak athletic performance or certain deficiency states induced by either inadequate nutrition or various diseases, ATP availability could prove to be a limiting step in actuating peak muscle output.

The importance of the compositions of the instant invention can be seen with the wide spread applications of such compositions.

Wound Healing:

According to the method of the invention, the composition(s) disclosed herein is applied to wound tissue in amounts sufficient to increase the healing rate of tissue. These compounds can significantly accelerate the rate of healing at nanomolar levels in vivo. For any given active agent, the optimum concentration for a given formulation may readily be determined empirically using no more than routine experimentation. In general, an amount of active agent suitable for use in accordance with the present invention ranges from about 0.001 µg to about 10 mg per kilogram body weight.

The compositions of the invention may be applied, preferably with a liposomal component.

In another preferred embodiment, the pharmaceutical compositions of the invention comprise the active ingredient, Coenzyme Q10, preferably in a pharmaceutical composition and a hydrogel. As will be appreciated by those skilled in the art, hydrogels are macromolecular networks that absorb water and thus swell but do not dissolve in water. That is, hydrogels contain hydrophilic functional groups that provide for water absorption, but the hydrogels comprise crosslinked polymers that give rise to aqueous insolubility. Generally, then, hydrogels comprise crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof.

If the composition is to be applied as a liquid, any type of application means may be employed which permits the influx of the active agents into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc.). Methods for the production of these formulations with the compounds of the present invention are apparent to those of ordinary skill in the art. If the compositions are to be delivered in a liquid form, preferably, a matrical or micellar solution is employed with the active agent present in a concentration range of from 1 ng/ml-5,000 µg/ml, from 10-500 µg/ml or 30-500 µg/ml. A preferred concentration range that is convenient will be at least 30 µg/ml. A particular matrical solution is a semi-solid polyethylene glycol polymer sold under the trademark HYDRON by Hydro Med Sciences, New Brunswick, N.J. Another preferred solution is a micellar solution sold under the trade name PLURONICS F108 by BASF, Ludwigshafen, Germany. Under room temperature conditions, this solution is a liquid, but when applied to warn tissue the solution forms a gel which permits the infusion of active agent into the wound tissue for a period of several days. Other preferred formulations include carboxymethyl cellulose preparations, crystalloid preparations (e.g., saline, Ringer's lactate solution, phosphate-buffered saline, etc.), viscoelastics, polyethylene glycols, polypropylene glycols and wound dressings (e.g., bandages, etc.).

The healing effects of the compounds of the present invention may be provided in a variety of instances. The lotion, cream, ointment, etc may be applied topically to surface wound tissue in the treatment of ulcers, lesions, injuries, diabetic ulcers, burns, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to closing the surgical site in order to accelerate internal capillary perfusion and healing. In addition, the rate of localized healing may be increased by the subdermal administration of active agent by injection or otherwise.

Muscle Pain, Pain and Joint Pain:

Often muscle soreness and joint pain occur concurrently as a result of physical exertion or old age. In addition, joint pain may occur as a result of arthritis or other degenerative joint diseases, which may also indirectly cause muscle soreness. Muscle and joint soreness occur in most mammals and, in particular, occur in humans, horses, dogs, and cats. The soreness creates many problems, such as making normal mammalian actions difficult and painful. These actions include walking, squatting, running, grasping, etc. To alleviate this discomfort, multiple pain relievers need to be taken, e.g., one pain reliever to address the muscle soreness and another pain reliever to address joint soreness. Multiple pain relievers, e.g. pills or tablets, can be difficult to administer in same mammals, such as horses, dogs, and cats. Further, there are significant costs associated with purchasing multiple pain relievers.

The compositions of the invention provide a cheap and effective way in the management of pain. See, the examples which follow.

Preferably, the compositions are administered on a as needed basis. The compositions can include penetrants to enable deep tissue penetration. However, compositions may be administered using any amount and any route of administration effective for decreasing muscle and joint soreness. Thus, the expression "amount effective to reduce sore muscles and joints", as used herein, refers to a nontoxic but sufficient amount of the composition to provide the desired reduction in muscle and joint soreness. The exact amount required will vary from host to host, depending on the species, age, size, weight, and general condition of the individual host, the severity of the soreness, the particular chemical formulation and its mode of administration, and the like.

The present compositions may be used to treat pain associated with many conditions by topically applying the compositions to the area of pain. Specifically, the compositions herein may be used to treat pain, including, but not limited to, arthritis, pain associated with cancer, neck pain, shoulder pain, back pain, surgical pain, preoperative and postoperative pain, temporal mandibular joint syndrome, carpal tunnel syndrome, and bone injury pain.

The compositions herein may also be used to treat pain associated with osteoarthritis, auto-immune diseases such as rheumatoid arthritis and psoriatic arthritis, gout, pseudo gout, ankylosing spondylitis, juvenile arthritis, systemic lupus erythematosus, arthritis associated with an infection, scleroderma and fibromyalgia.

In addition, the compositions herein may be used to treat muscle pain, pain associated with muscle tension, fatigue, curvature of the spine, minor and major spinal disc compression, pinched nerves, strained or sprained muscles, and nervous tension.

Moreover, the present compositions may be used to treat pain associated with traumatic injuries, hematomas, myositis, lower back syndromes, spinal stenosis, joint pain, bone pain and bone fractures caused by metastatic cancer, such as breast, lung, or prostrate cancer. Other cancers that can cause such pain include sarcomas and osteosarcomas. The present composition may also be used to treat muscle, bone and joint pain generally associated with cancer.

The present compositions may be used to treat pain associated with osteoprotic fractures of the lumbar spine and other sites, and traumatic bone fractures, including pelvic fractures. With respect to joint pain, the compositions herein may be used to decrease overall joint stiffness and increase joint mobility.

The present compositions may also be used to treat pain associated with pre-surgical and post-surgical orthopedic procedures. For example, the present compositions may be applied to treat such pain before or after arthroscopy, especially in the shoulders or knees.

In addition, the present compositions may be used for treating pain associated with post-surgical orthopedic recovery, such as tendon, muscle and bone repair, as well as joint replacement, including hip or knee replacement. For example, bone fractures require the use of plates, screws or other attachment means to hold the bones together. Placement of these devices requires surgery, and the post-surgical pain resulting therefrom can be treated with the present compositions.

Further, the compositions herein may be used to treat pain caused by herniated nucleus pulposus (slipped disc), musculo-skeletal pain, joint dislocations, herniated intervetebral disc, prolapsed intervetebral disc (including lumbar and cervical), ruptured disc, whiplash injuries, fibromyositis, intercostal rib pain, muscle tear, tendonitis, bursitis, meniscal tears, tendon tears, and bone spurs. The compositions herein may also be used to treat pain such as cervical muscle hyperactivity (spasm), an extremely common condition with many causes, including tension, response to an inflamed or subluxed joint, arthritic changes, poor posture or work habits, trauma, systemic disease and adjacent pathology.

The compositions of the present invention may be used to treat pain caused by sports related injuries. Such sports-related injuries include, but are not limited to, hematomas, bruises, sprains (e.g., ankle sprain), muscle spasms (e.g., pulled muscles), partial tendon tears, tendonitis, bursitis, myositis, traumatic arthritis and post-insertion of joint dislocation. In treating pain associated with sports related injuries, the present compositions would be applied to the area of pain as described herein. The present compositions may be used in combination with sports-injury therapy techniques such as physical therapy, acupuncture, weight-training, biofeedback techniques, among others.

The present compositions may also be used in treating pain unique to senior citizens. Much of the bone, joint or muscle pain experienced by seniors results from a combination of sources. Some of these sources are known, others are not. In certain cases, such pain is a natural consequence of the diseases resulting from the aging process, which includes pain accompanied with diminished motor function, atrophy, dietary changes, among others. Consequently, pain management in seniors is difficult. Often times, seniors are required to take multiple medications daily in order to effectively manage their pain. This poses significant drawbacks to seniors, such as side effects from the medications, adverse reactions in mixing the medications, as well as excessive costs and effort to maintain the required medication regimen on a daily basis.

Thus, using the present compositions to treat bone, joint or muscle pain in seniors can be effective in minimizing the amount of pain relief medication they already take, or would be required to take in the future. Also, pain in seniors contributes to depression, inactivity and immobility in this age group. Diminution in pain resulting from use of the present compositions would result in greater independence, increased activity, socialization, appetite and overall sense of well-being in an elderly patient.

In addition, the compositions of the present invention can be utilized as an adjunct to physical therapy. Generally, physical therapy involves passive and active treatments or methodologies to strengthen and/or heal muscles, tendons, bones, and joints. The draw backs of physical therapy include pain and discomfort to the patient. The formulations of the present invention can be used to treat such pain. For example, the present formulation may be applied to the area of pain (as described herein) before, during, and/or after each physical therapy treatment.

The present compositions can also be used to treat pain associated with immobilized tissue. Treatment of damaged muscles, bones, tendons, and joints often requires that tissues be immobilized for an extended period of time. In these circumstances, the tissue is kept immobilized by a variety of devices including, but not limited to, braces, slings, casts, bandages and splints. Oftentimes, when the device is removed and continuing thereafter, the patient experiences muscle, bone, tendon and/or joint pain in or about the immobilized area. The present formulation can be used to treat such pain by applying the formulation to the area of pain in the manner described herein.

TENS or transcutaneous electro-nerve stimulation is characterized by high voltage, sensory current and is used to block pain. The present compositions can be used in conjunction with electrical neuromuscular stimulation to increase the effectiveness of the pain treatment. For example, before or after treatment with electrical neuromuscular stimulation, the present composition can be applied to the affected area in the manner described herein.

The present composition can also be used in combination with local or other injections of an anesthetic, such as lidocane (with and without steroids). For example, a needle containing lidocane (with or without a steroids) can be injected into the skin overlying the area of pain. This area of the skin can be further anesthetized by applying the present composition at or around the injection site before or after the injection.

In addition, the present composition may be used in combination with oral analgesics or anti-inflammatories (e.g., NSAIDS and Cox-2-inhibitors) to alleviate pain. When used in such manner, for example, the composition herein can provide an enhanced and/or additive pain relief effect.

The present composition may also be used in combination with heat treatment devices including, but not limited to, hot packs such as heating pads or hot towels. Such devices may also include Diathermy which is a deep tissue heat treatment, wherein the temperature of the injured tissues is raised by high frequency current, ultrasonic waves, or microwaves radiation. Diathermy is used to reduce pain, relieve muscle spasm, decrease soft-tissue contractures, resolve inflammation, and promote healing. The present compositions can be used in combination with hot packs or Diathermy to provide an enhanced and/or additive relief effect.

Further, the present composition may be used in combination with morphine-like agents, such as codeine, opiates, oxy-contin, Percocet, Demorol, and Vicadin. When used in such manner, for example, the morphine-like agents, together with any of the formulations of the present invention, can achieve an analgesic effect that would otherwise require a higher dosage of opioids but with fewer side effects.

In addition, the present composition may be used in combination with biofeedback techniques. Biofeedback is a useful technique for achieving stress reduction, reducing anxiety and alleviating psychosomatic symptoms by monitoring and controlling certain physiological processes. The use of biofeedback techniques in combination with the compositions herein may allow the patient to achieve greater control over his or her physiological processes and to achieve greater reduction in pain than through the use of such techniques.

The present compositions can also be used in combination with acupuncture therapy. Acupuncture therapy generally involves inserting tiny needles at certain specific points on the surface of the body. Acupuncture has proven efficacy in relieving pain. Acupuncture may also be useful for the treatment of osteoarthritis, low back pain, carpal tunnel syndrome, fibromyalgia, and other conditions that cause chronic pain. The compositions herein may provide an enhanced and/or additive relief effect when used in combination with acupuncture.

Pain associated with cancer is one of the most severe forms of pain. Such pain can be further exacerbated by cancer treatments, including radiation therapy and chemotherapy. The present compositions may be used to treat cancer associated pain in muscles, bones, and joints. The present compositions can also be used in combination with currently available treatments for such pain to provide an enhanced and/or additive relief effect.

Utilizing the present compositions to reduce pain in cancer patients would bring about, for example, improved mood and motivation of the patient, as well as pain relief from the cancer itself and the pain brought about by the patient's continued cancer therapy treatments. Also, when treated in such a manner, the patient may experience improved mobility, thus increasing the patient's chances for successfully conducting daily activities and improving the patient's overall well being. By using the compositions herein, the patient may also experience greater flexibility in going to and from cancer treatment sessions.

Kits

In a preferred embodiment, the invention provides kits comprising CoQ10 compositions for the treatment of wounds, pain, fatigue and the like. Transdermal, oral and intravenous preparations of 2,3-dimethoxy-5-methyl-6-decaprenyl-1,4-benzoquinone (coenzyme Q-10) comprise, inter alia, auxiliary agents, an effective amount of pulmonary surfactant, and/or in combination with liposomes.

In a preferred embodiment, the CoQ10 compositions can further comprises CoQ10, liposomes, and a pharmaceutically acceptable carrier. Preferably, the composition comprises between about 0.001% to about 60% (w/w) of Coenzyme Q10.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1: An In Vitro Study to Test its Effect on Smooth Muscle Cell Proliferation and ATP Production of the Active Ingredient Q10

The composition is a topical formulation containing phospholipid liposomes that encapsulate the intracellular energy producer, Coenzyme Q10 (Q10). The data show a direct correlation between Q10 used in our topical formulation and energy production.

We have investigated the effect of Q10 on ATP production in Human Aortic Smooth Muscle Cells (HASMC). This cell line was chosen for the study based on its ability to produce ATP at levels detectable by the Luciferin-Luciferase ATP assay. We also studied the effect of The composition comprising about 0.001% to about 60% (w/w) Coenzyme Q10 on Muscle Cell proliferation. The data show that Q10 supplies ATP to the proliferating muscle cells.

Human Aortic Smooth Muscle Cells (HASMC) were obtained from the American Type Culture Collection, (ATCC, Richmond, Va.) at P16 in a cyro-vial. Medium 231, Trypsin-EDTA, Defined Trypsin Inhibitor, DTI, PSA solution (Penicillin, Streptomycin, and Amphotericin B) and SMGS were all obtained from Cascade Biologics™ (Portland, Oreg.). D-(+)-Glucose, Coenzyme Q10, Butylated Hydroxytoluene (BHT), Sodium Phosphate, Glycerol, and Trichloroacetic Acid (TCA) were all obtained from Sigma-Aldrich®, (St. Louis, Mo.). Phosholipon 90 (95% phospholipids) was obtained from American Lechitin Company (Oxford, Conn.). Medium Chain Tryglyceride (MCT) was obtained from Johnson & Johnson (Evansville, Ind.). The ATP Assay kit was obtained from Calbiochem®, (San Diego, Calif.) and the 75 $cm^2$ and 6-well culture plate were attained from Corning®, (Atlanta, Ga.).

Culture of HASMC:

The vial was frozen in liquid Nitrogen upon receipt until the initiation of a culture. The contents of the vial were mixed with Medium 231 and SMGS after defrosting in a water bath. The cultures (P16-P20) were maintained in 75 $cm^2$ culture flasks. Cultures were incubated at 37° C. using carbonate and HEPES buffered Medium 231 (pH 7.4) under humid conditions at 5% $CO_2$. The media was supplemented with SMGS containing 5% serum, other growth supplements and a 500×PSA solution.

Cell Preparation:

At approximately 80% confluency, the cells were subcultured using Trypsin-EDTA to detach the cells and Defined Trypsin Inhibitor, DTI to neutralize the cell suspension before centrifugation at 2500 RPM for 8 minutes. The supernatant was aspirated and discarded. The resultant cell pellet was then resuspended in fresh Medium 231. A cell count was performed using a hemocytometer before seeding the experimental 6-well plates at 200,000 cells/well.

Reagent Preparation:

Q10 was dissolved in ethanol and the solution was diluted with Medium 231 to the required concentrations. The Vehicle used in preparing the composition comprising about 0.001% to about 60% (w/w) Coenzyme Q10 was composed of MCT, BHT, Glycerol, and Sodium Phosphate buffered to pH 7.2 and subjected to sonication, then diluted with Medium 231 to experimental concentrations.

Experimental Set-Up:

D-(+)-Glucose at 10 mM (Peiro et al., *Brit. Jour. of Pharmacology* 133: 967-974 (2001)) was used as an energy substrate for the production of ATP. The wells of the 6-well plate were incubated with 0-20 µg/ml of CoQ10, 1 µg and 20 µg/ml CoQ10, or 1 µg and 20 µg/ml of the Vehicle of Coenzyme Q10, all in Medium 231. The well plates were incubated at 37° C. and 5% $CO_2$ for specified experimental periods. Medium 231 contains 4.6 mM Glu originally, thus only an additional 5.4 mM added to medium (Dr. Gary D. Shipley, Cascade Biologics, Portland, Oreg.).

Cell Counts:

The well-plates were decanted to empty the wells of the reagents and any residue was aspirated carefully with an electronic pipettor. 0.5 ml Trypsin-EDTA was added to each well for 5-7 minutes to aid detachment. Upon complete detachment as determined under a microscope, 0.5 ml Medium 231 was added to the resultant cell suspension to neutralize the Trypsin. 0.5 ml of this cell suspension was taken for reading in a Coulter cell counter.

ATP Assay:

After incubation, the medium was removed and replaced with cold (4° C.) 1% w/v Trichloroacetic Acid (TCA) as the lysis buffer. This buffer causes almost instantaneous inhibition of ATPases (Kangas et al., *Med Biol* 62: 338-343 (1984)). The wells were incubated with TCA at room temperature for 5 min with gentle swirling. Each well was then scraped to dislodge attached cells and formulate a cell lysate suspension. The lysates in each well were pipetted up and down a few times to form a uniform suspension. Samples were taken from each well and an ATP Assay was performed according to manufacturer's instructions in a Berthold® Luminometer (Bundoora, Australia).

Data Analysis:

The results were analyzed for statistical significance by ANOVA using the software SigmaStat™. Posthoc comparisons were made using Dunnett's test with alpha set at 0.05.

Results:

HASM Cells were incubated at 37° C. and 5% $CO_2$ with 0-20 µg/ml Coenzyme Q10. The 6-well plates were incubated for 24 h in Medium 231. After treatment with cold TCA cell lysis buffer and gentle scraping, cells were mixed by pipetting. Samples were then taken for quantification of ATP using the Luciferin-Luciferase ATP Assay. (FIG. 1; *Significant compared to Ctrl, $P<0.05$, One-way ANOVA and Dunnett's).

Figure 2:
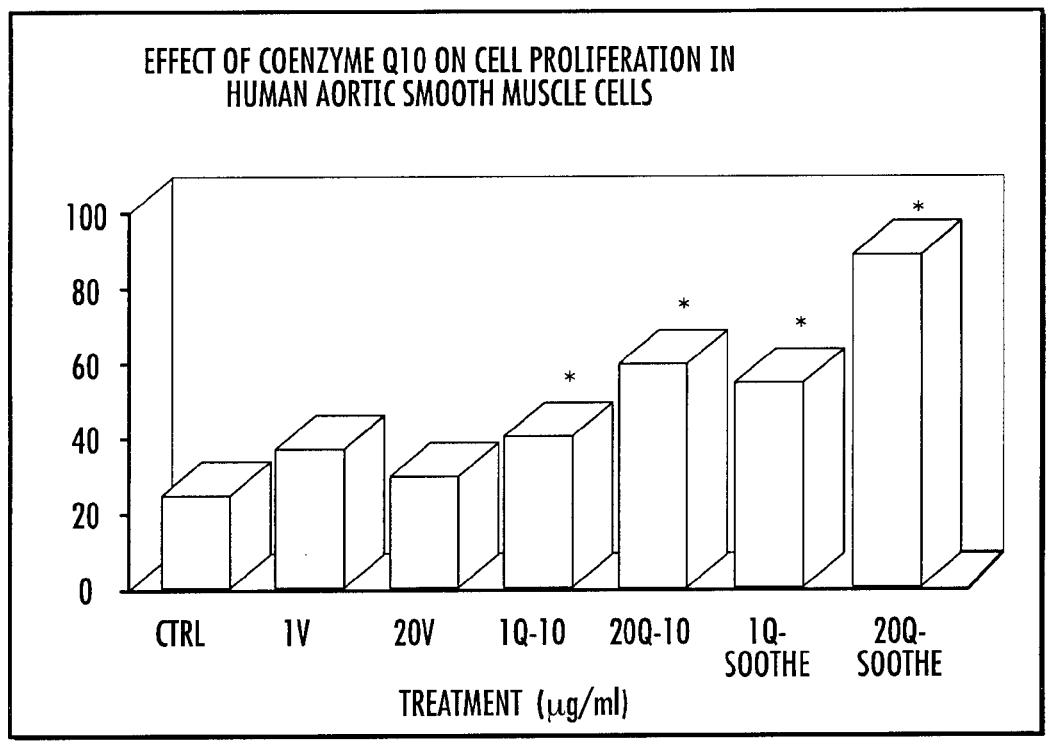
FIG. 2 is a graph showing the effect of coenzyme Q10 on cell proliferation in human aortic smooth muscle cells. *Significant compared to Ctrl, P<0.05; One-way ANOVA and Dunnett's.

In FIG. 2, HASM Cells were incubated at 37° C. and 5% $CO_2$ with 0-20 µg/ml Coenzyme Q10, The composition comprising about 0.001% to about 60% (w/w) Coenzyme Q10, and the Vehicle(V) used in The composition comprising about 0.001% to about 60% (w/w) Coenzyme Q10. The 6-well plates were incubated for 24 h in Medium 231. After treatment with Trypsin-EDTA and gentle scraping, cells were neutralized with Medium 231 and mixed by pipetting. Samples were then taken for quantification using a Coulter cell counter. (*Significant compared to Ctrl, $P<0.05$; One-way ANOVA and Dunnett's).

TABLE 1

| Treatment (µg/ml) | Cell number ($10^4$) | % Diff vs. Ctrl (24 hr) |
|---|---|---|
| CTRL | 25.7 | N/A |
| 1.0 Vehicle | 38.5 | 49.8% |
| 20.0 Vehicle | 40.0 | 55.6% |
| 1.0 Q-10 | 42.4 | 65.1% |
| 20.0 Q-10 | 63.1 | 145.6% |
| 1.0 Q-Soothe | 57.6 | 124.20% |
| 20.0 Q-Soothe | 94.6 | 268.0% |

Figure 3:
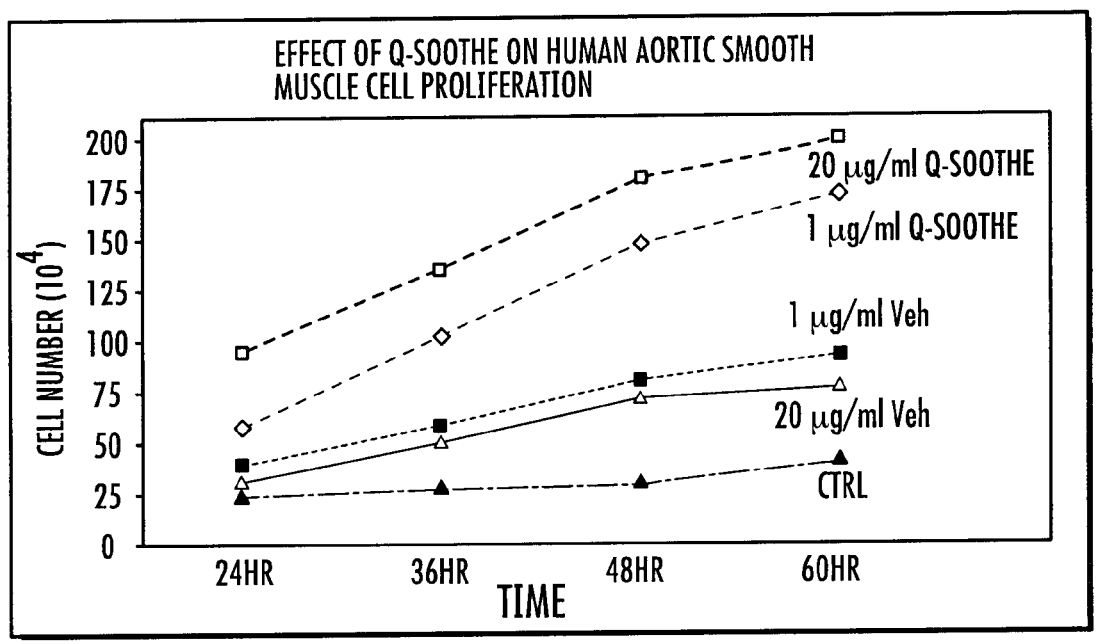
FIG. 3 is a graph showing the effect of the composition comprising between about 0.001% to about 60% (w/w) of Coenzyme Q10 on human aortic smooth muscle cell proliferation. *Significant compared to Ctrl, P<0.05; One-way ANOVA and Dunnett's.

FIG. 3: HASM Cells were incubated at 37° C. and 5% $CO_2$ with 0-20 µg/ml, The composition comprising about 0.001% to about 60% (w/w) Coenzyme Q10. The 6-well plates were incubated for 24-60 hr in Medium 231. After treatment with Trypsin-EDTA and gentle scraping, cells were neutralized with Medium 231 and mixed by pipetting. Samples were then taken for quantification by a Coulter cell counter. (*Significant compared to Ctrl, $P<0.05$; One-way ANOVA and Dunnett's).

These results indicate that Coenzyme Q10 has a stimulatory effect on ATP production in HASMC. The data indicate a correlation between increased concentration of Q10 and higher levels of cellular ATP production in these cells. We further tested the effect of Q10 on proliferation of HASMC. As presented in FIG. 2, incubation with the compositions led to higher levels of proliferation as compared to the Vehicle or control.

Taken together, the data suggest that Q10 administration to human aortic smooth muscle cells increases ATP production and implies that the phospholipid vehicle is effective in delivering exogenous Q10 to cells. Given the aforementioned, a topical formulation of Q10 would be able to facilitate delivery of Q10 to the underlying dermal vasculature and drive ATP production. Moreover, Q10 is potent antioxidant and would also act as a free radical scavenger and reduce the oxidative stress related to fatigued muscles and sore joints.

Example 2: To Examine the Effect of the Composition on Deep Partial Thickness Wound Healing The objective of this study was to examine the effect of the CoQ10 composition on deep partial thickness wound healing in a porcine model.

Experimental Animals:

A porcine model was used for our experimental research due to the morphological similarities between swine skin and human skin. Two young female specific pathogen free (SPF: Ken-O-Kaw Farms, Windsor, Ill.) pigs weighing 25-30 kg were kept in house for two weeks prior to initiating the experiment. These animals were fed a basal diet ad libitum and were housed individually in our animal facilities (meeting American Association for Accreditation of Laboratory Animal Care [AAALAC] compliance) with controlled temperature (19-21° C.) and lighting (12 h/12 h LD).

The experimental animal protocols used for this study are approved by the University of Miami Institutional Animal Care and Use Committee and all the procedures followed the federal guidelines for the care and use of laboratory animals (U.S. Department of Health and Human Services, U.S. Department of Agriculture). The studies were conducted in compliance with the University of Miami's Department of Dermatology and Cutaneous Surgery Standard Operating Procedure (SOPs). Animals were monitored daily for any observable signs of pain or discomfort. In order to help minimize possible discomfort, an analgesic buprenorphine 0.03 mg/kg (Buprenex injectable; Reckitt Benckiser Hull, England) was given to each animal on the first day, and every third day thereafter, while under anesthesia; a fentanyl transdermal system: 25 μg/hr (Duragesic; Alza Corp. Mountain View, Calif.) was used during the entire experiment.

Wounding Technique:

The flank and back of experimental animals was clipped with standard animal clippers on the day of the experiment. The skin on both sides of each animal was prepared for wounding by washing with a non-antibiotic soap (Neutrogena Soap Bar; Johnson and Johnson, Los Angeles, Calif.) and sterile water. Each animal was anesthetized intramuscularly with tiletamine HCl plus zolazepam (1.4 mg/kg) (Telazol; Laderle Parenterals Inc, Carolina, Puerto Rico), xylazine (2.0 mg/kg) (X-jet; Phoenix Scientific Inc, St. Joseph, Mo.), and atropine (0.04 mg/kg) (Atrojet SA; Phoenix Scientific Inc, St. Joseph, Mo.) followed by mask inhalation of an isoflurane (Isothesia; Abbott Laboratories, Chicago, Ill.) and oxygen combination.

Approximately 90 rectangular wounds measuring 10 mm×7 mm×0.5 mm deep were made in the paravertebral and thoracic area with a specialized electrokeratome fitted with a 7 mm blade. The wounds were separated from one another by approximately 15 mm of unwounded skin.

Figure 4:
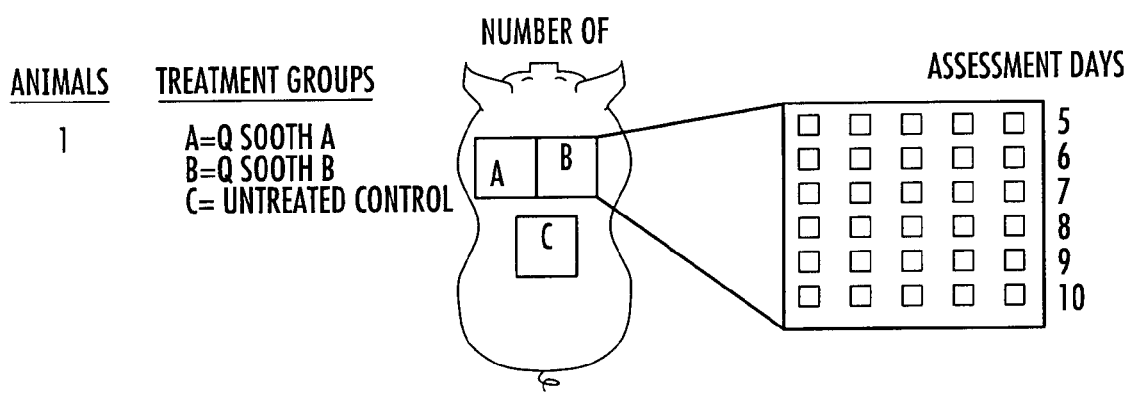
FIG. 4 is a schematic illustration of the experimental design for treatment in animals.

Treatments:

Thirty (30) wounds will be randomly assigned to each treatment group according to the experimental design shown in FIG. 4. Wounds will be treated with their respective topical ointments once a day for five days.

Figure 5:
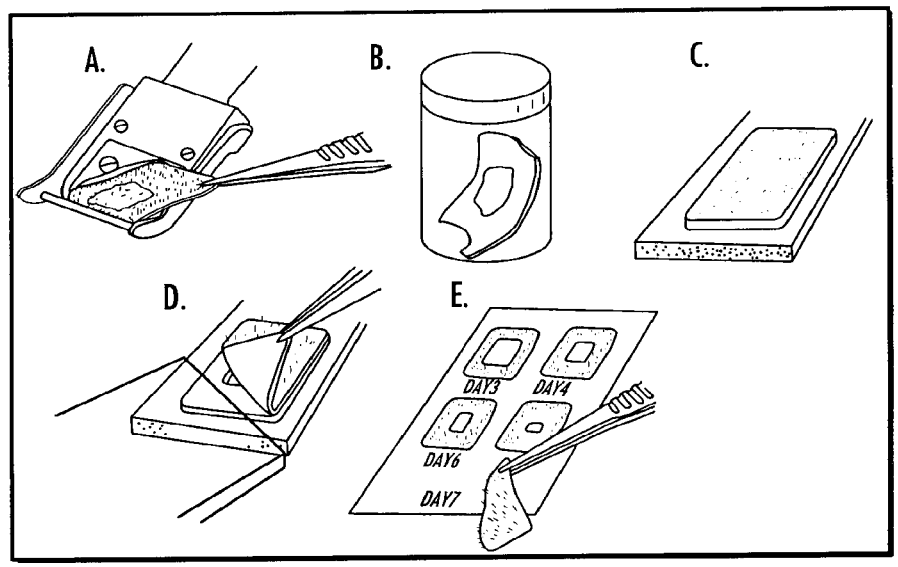
FIG. 5 is a schematic illustration showing the epidermal migration assessment diagram.

Epidermal Migration Assessment:

Beginning on day 5 after wounding (Day 0), and on each day thereafter for up to five days, five (5) wounds and the surrounding normal skin from each treatment group were excised using electrokeratome with a 22 mm blade set at a depth of 0.7 mm. All specimens that were not excised intact were discarded. The excised skin containing the wound site was incubated in 0.5 M sodium bromide at 37° C. for 24 hours, allowing for a separation of the dermis from the epidermis (see diagram). After separation, the epidermal sheet was examined macroscopically for defects. Defects are defined as holes in the epidermal sheet or as a lack of epidermal continuity in the area of the wound. Epithelization is considered complete (healed) if no defect(s) is present; any defect in the wound area indicates that healing is incomplete. The mounted samples were retained for a permanent record. FIG. 5 is a schematic illustration showing the epidermal migration assessment diagram.

Figure 6A:
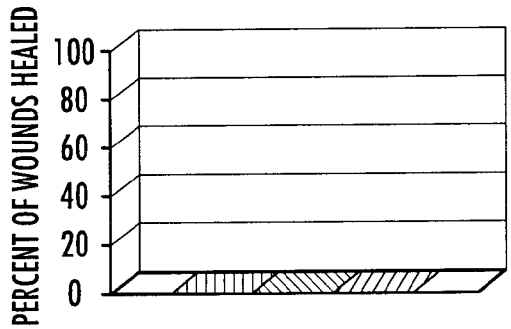
FIGS. 6A-6E are graphs showing the effects of the composition comprising about 0.001% to about 60% (w/w) Coenzyme Q10 on wound healing. On day 5, shown in FIG. 6A, none of the wounds in any treatment group were completely re-epithelialized. Day 6 (FIG. 6B), eighty percent (80%) of the wounds from the group treated with CoQ 10 A were completely re-epithelialized, as compared to twenty percent (20%) for those treated with CoQ 10 B, and no wounds from the untreated group. Day 7 (FIG. 6C), one hundred percent (100%) of the wounds treated with CoQ A and with CoQ B were completely re-epithelialized as compared to zero percent of wounds from the untreated group. Day 8 (FIG. 6D) one hundred percent (100%) of the wounds treated with CoQ A and with CoQ B were completely re-epithelialized as compared to zero percent of wounds from the untreated group. Day 9 (FIG. 6E), all wounds in each treatment group were completely re-epithelialized.
Figure 6B:
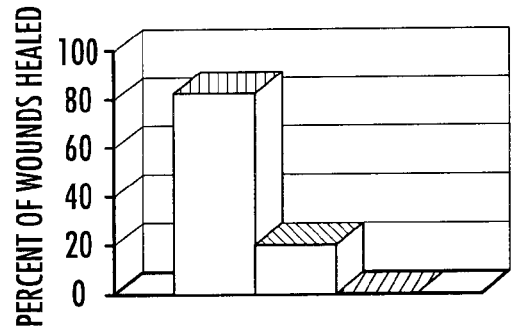
Figure 6C:
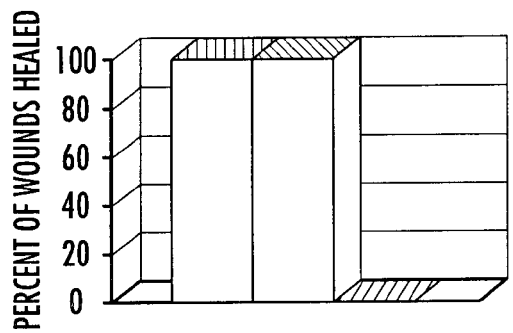
Figure 6D:
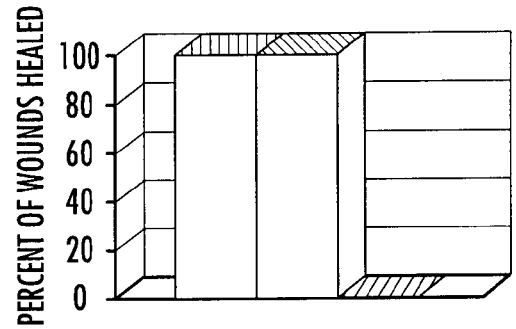
Figure 6E:
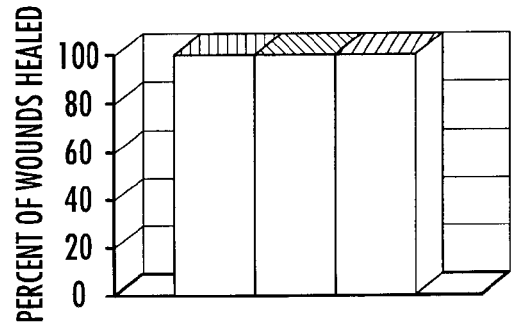

Results: On day 5, shown in FIG. 6A, none of the wounds in any treatment group were completely re-epithelialized. Day 6 (FIG. 6B), eighty percent (80%) of the wounds from the group treated with CoQ A (1% w/w Coenzyme Q10) were completely re-epithelialized, as compared to twenty percent (20%) for those treated with CoQ B (placebo), and no wounds from the untreated group. Day 7 (FIG. 6C), one hundred percent (100%) of the wounds treated with CoQ A and with CoQ B were completely re-epithelialized as compared to zero percent of wounds from the untreated group. Day 8 (FIG. 6D) one hundred percent (100%) of the wounds treated with CoQ A and with CoQ B were completely re-epithelialized as compared to zero percent of wounds from the untreated group. Day 9 (FIG. 6E), all wounds in each treatment group were completely re-epithelialized.

TABLE 2

Re-epithelization Results

| Treatment Group | Days After Wounding | | | | |
|---|---|---|---|---|---|
| | 5 | 6 | 7 | 8 | 9 |
| Q-Sooth A | 0/5 (0%) | 4/5 (80%) | 5/5 (100%) | 5/5 (100%) | 5/5 (100%) |
| Q-Sooth B | 0/5 (0%) | 1/5 (20%) | 5/5 (100%) | 5/5 (100%) | 5/5 (100%) |
| Untreated | 0/5 (0%) | 0/5 (0%) | 0/5 (0%) | 0/5 (0%) | 5/5 (100%) |

Example 3: Coenzyme Q10 Enhances the Proliferation and Migration of Fibroblasts and Keratinocytes: Implications for Wound Healing The proliferation and migration of keratinocytes and fibroblasts are paramount to the restoration of the cutaneous architecture. Studies have suggested that Coenzyme Q10 (Q10) protects normal cells when exposed to apoptotic stimuli (e.g. serum deprivation, UV irradiation, etc.). Q10 is a potent antioxidant essential in the production of ATP via oxidative phosphorylation in mitochondria and has been shown to increase ATP production in a variety of cell types. To test the effect of Q10 on neonatal fibroblasts and keratinocytes, an in vitro incisional wound model was employed. Cells were seeded in 6-well tissue culture plates with supplemented media and incubated for 48 hours to facilitate a 90% confluency level prior to experimentation. A cross-shaped "wound" gap was made among the near confluent monolayer of cells in the center of each well. Detached cells were then washed off with medium. Each well was then replenished with medium with or without Q10. The cell cultures were examined and images captured using a Zeiss Axiovert 200 inverted microscope with a digital camera at various time intervals. The center of the cross was used for positioning of the gap. Cell migration was quantified by time and percentage of "wound" gap covered by cells that migrated into the gap field. The percentage of gap filled (PGf) was calculated as $PGf=(1-At/A0)\times 100$, where At is the gap area at time t, and A0 is the gap area at time 0. Statistical analysis was performed using the student's t-test. The data indicate a statistically significant increase in the rate of gap coverage in the treated group versus control. These data suggest that Q10 may be supportive in wound healing and sets a template to warrant further investigation.

Methods:

Human neonatal fibroblasts (nFIB) and human neonatal keratinocytes (SC-KC) were grown to ~90% confluency in T-75 flasks at which time they were trypsinized and seeded into 6-well tissue culture plates. The plates were incubated at 37° C. under humidified conditions and 5% $CO_2$. Upon reaching a 90% confluency level, a cross-shaped gap was made in each well to mimic an incisional wound using a P-200 pipette tip. The medium was changed to indicated treatments immediately after induction of cross signifying time 0. The cell cultures were examined and images captured using a Zeiss Axiovert 200 inverted microscope with a digital camera at various time intervals. Cell migration was quantified by time and percentage of "wound" gap covered by cells that migrated into the gap field. The percentage of gap filled (PGf) was calculated as $PGf=(1-At/A0)\times 100$, where A(t) is the gap area at time t, and A(0) is the gap area at time 0. Statistical analysis was performed using the student's t-test.

Figure 7:
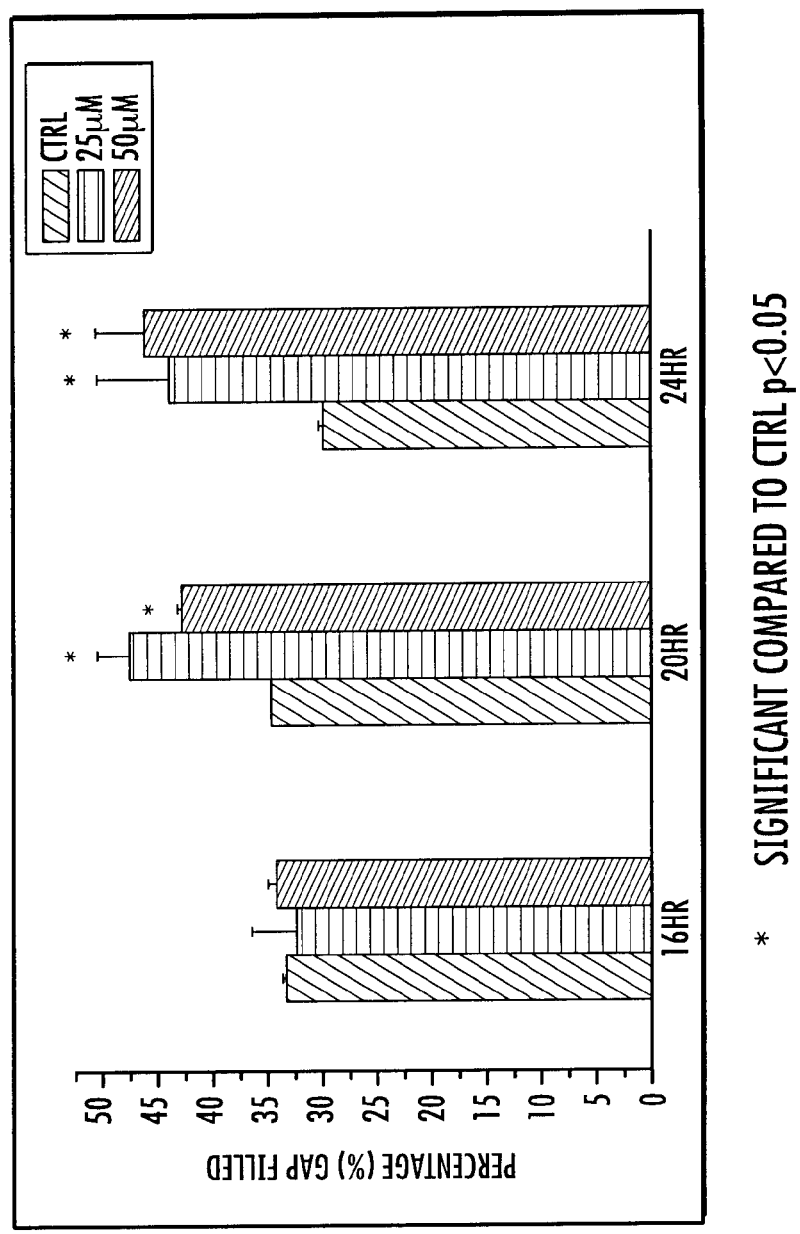
FIG. 7 is a graph showing the effect of Q10 on fibroblast migration.
Figure 8:
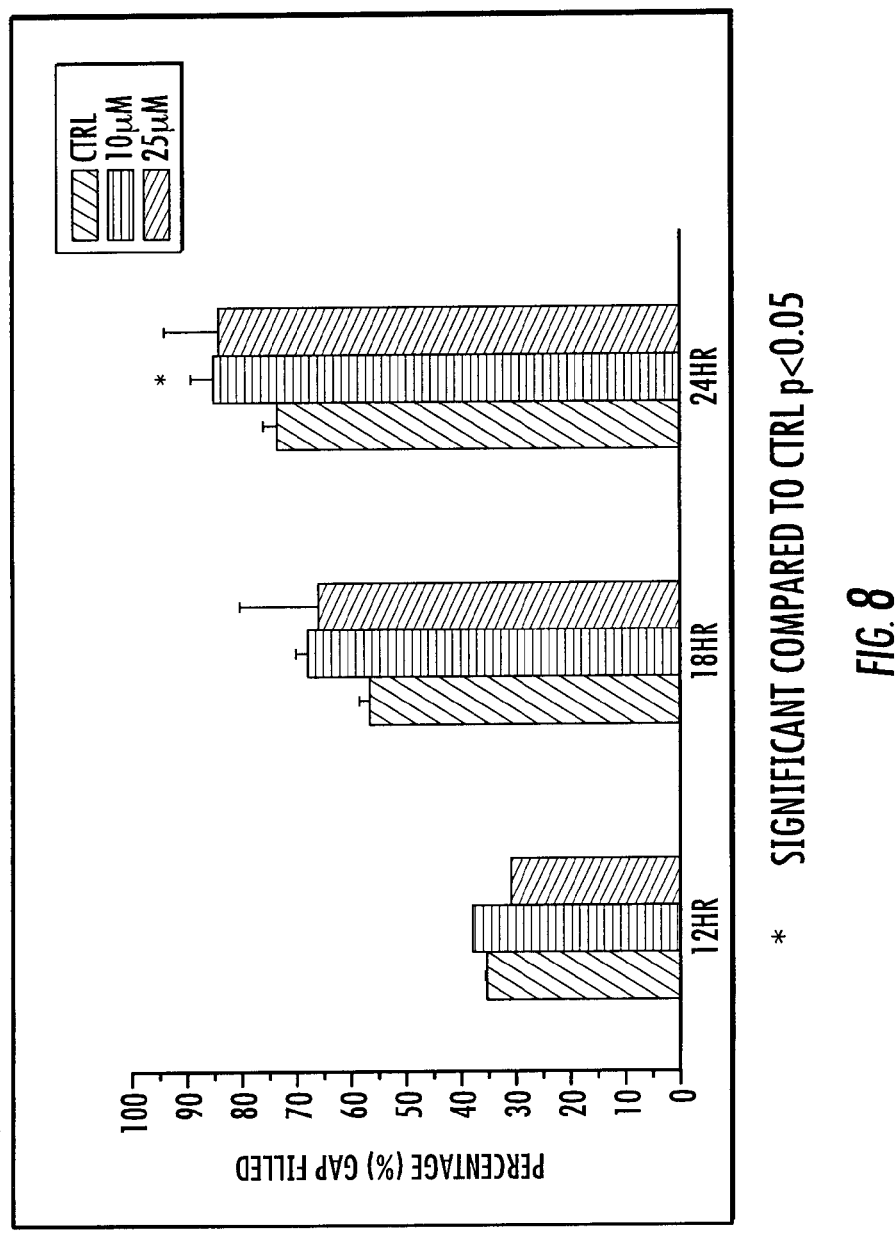
FIG. 8 is a graph showing the effect of Q10 on keratinocyte migration.
Figure 9:
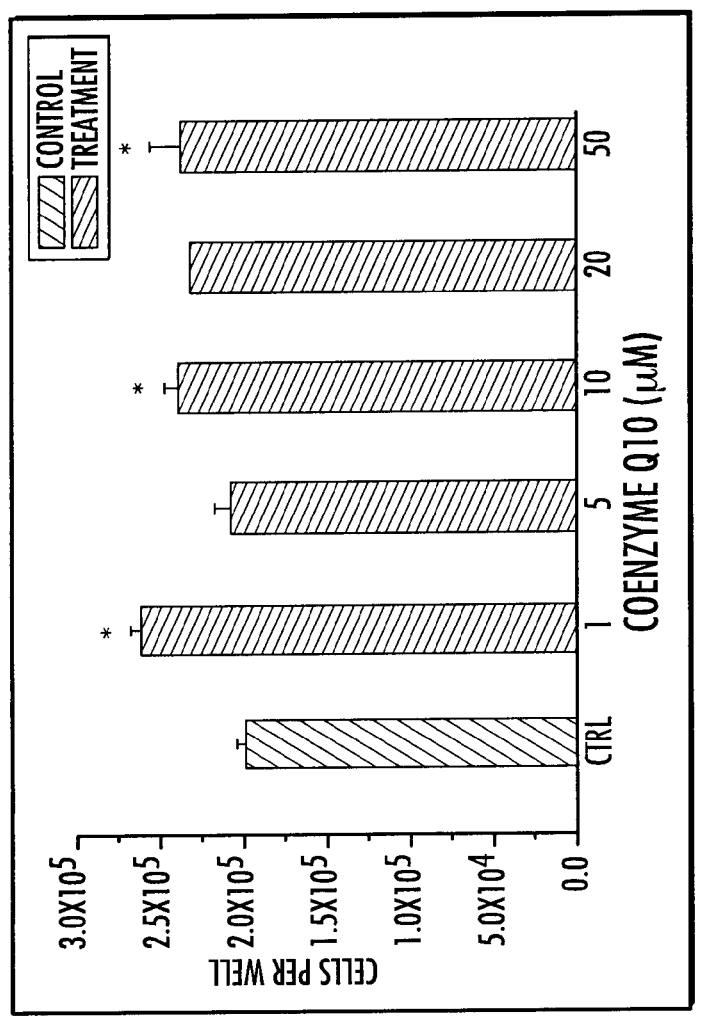
FIG. 9 is a graph showing the effect of Q10 on fibroblast proliferation.
Figure 10:
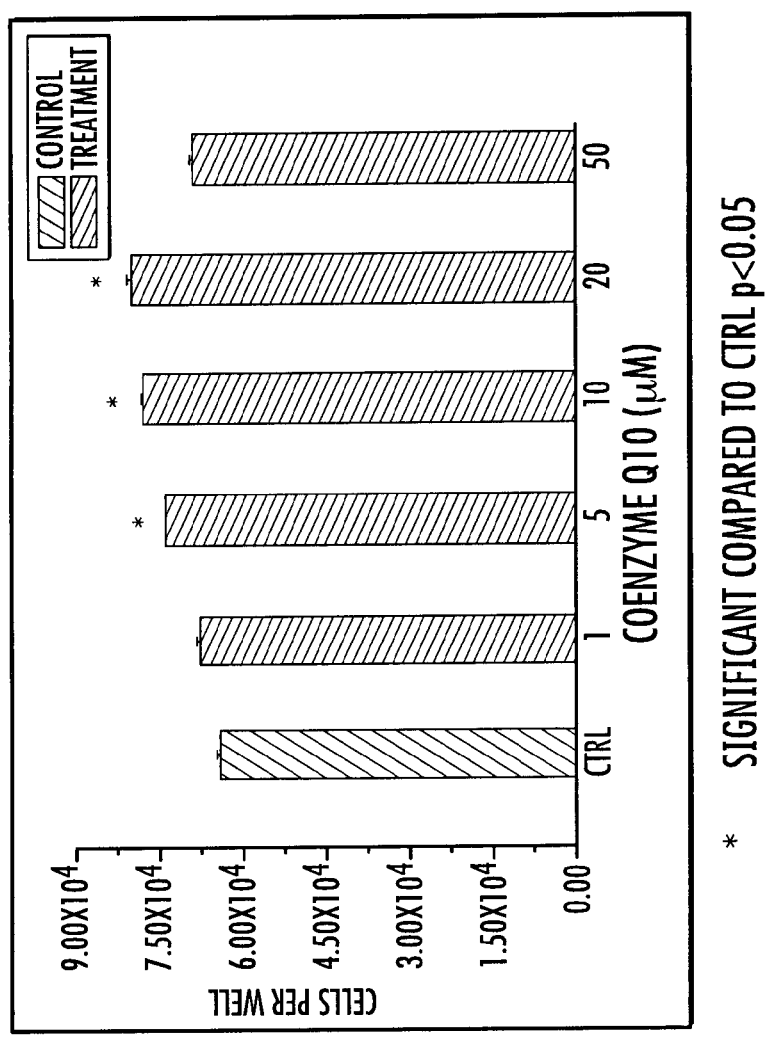
FIG. 10 is a graph showing the effect on keratinocyte proliferation.

FIGS. 7-10 show the results obtained. FIG. 7 shows the effect of Q10 on fibroblast migration; FIG. 8 shows the effect of Q10 on keratinocyte migration; FIG. 9 shows the effect of Q10 on fibroblast proliferation; FIG. 10 shows the effect on keratinocyte proliferation. These data suggest use of Coenzyme Q10 in wound healing and coenzyme Q10 enhances the migration and proliferation of normal keratinocytes and fibroblasts.

Figure 11:
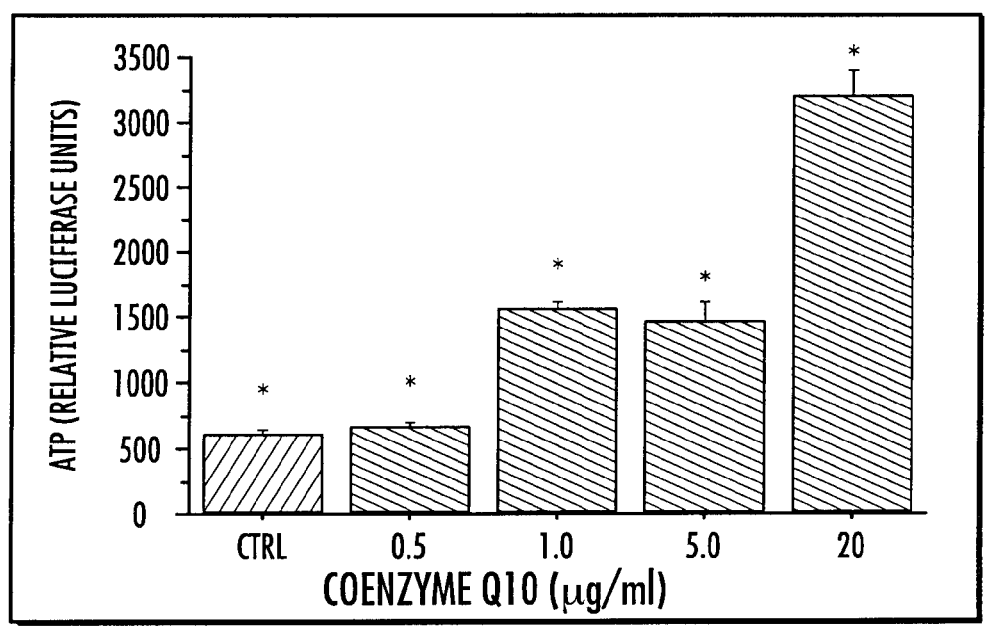
FIG. 11 is a graph showing the effect of coenzyme Q10 on ATP production in human aortic smooth muscle cells. *Significant compared Ctrl, P<0.05 (One-way ANOVA and Dunnett's method).

FIG. 11 shows the effect of coenzyme Q10 on ATP production in human aortic smooth muscle cells. Human Aortic Smooth Muscle Cells (HASMC) were incubated at 37° C. and 5% $CO_2$ with 0-20 µg/ml Coenzyme Q10. 6-well plates were incubated for 24 hr in Medium 231. After treatment with cold TCA cell lysis buffer, an ATP assay was performed using the Luciferin-Luciferase method. *Significant compared Ctrl, $P<0.05$ (One-way ANOVA and Dunnett's method).

In summary, CoQ10 potential effects on wound healing, include cellular proliferation and migration; increased ATP demand; changes in the prooxidant-antioxidant equilibrium; changes in cell and organelle membrane stability; and, apoptosis.

Example 4: CoQ10 Composition—Clinical Trial

Figure 12:
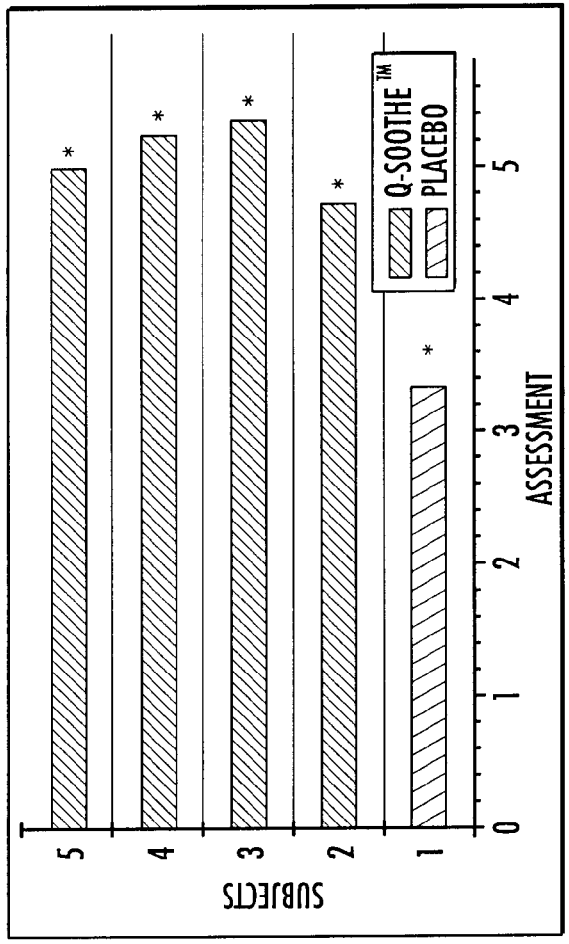
FIG. 12 is a graph showing an overall assessment of data obtained from the clinical study of the relief of pain after treatment with either CoQ10 composition or placebo.

This clinical trial is an IRB approved double blinded study at the University of Miami Athletic department. The CoQ10 composition is administered to subjects with joint pain or muscular fatigue. Each subject was assessed for improvement in pain, fatigue, soreness, and overall well-being. FIG. 12 is a graph showing an overall assessment of data obtained from the clinical study of the relief of pain after treatment with either CoQ or placebo.

Figure 13:
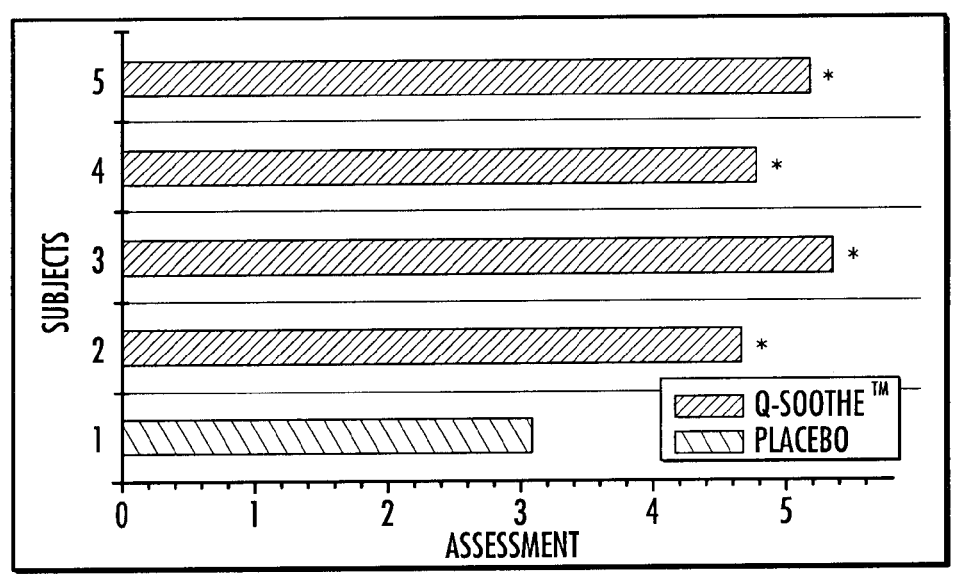
FIG. 13 is a graph showing the data from the clinical study of the relief of pain after treatment with either CoQ10 composition or placebo.

The Effect of CoQ10 Compositions on Relief of Pain:

This clinical trial is an IRB approved double blinded study at the University of Miami Athletic department. CoQ10 composition is administered to subjects with joint pain or muscle fatigue. Each subject was assessed for improvement in pain, fatigue, soreness, and overall well-being. FIG. 13 shows the preliminary data from the clinical study of the relief of pain after treatment with either CoQ10 composition or placebo.

OTHER EMBODIMENTS

It is to be understood that while the invention has been described in conjunction with the detailed description thereof, the foregoing description is intended to illustrate and not limit the scope of the invention. Other aspects, advantages, and modifications are within the scope of the following claims.

What is claimed is:

1. A method of accelerating re-epithelialization of a partial thickness wound, comprising administering a topical composition comprising a therapeutically effective amount of CoQ10 and liposomes, wherein the composition comprises between about 0.001% and about 60% (w/w) of CoQ10, and a pharmaceutically acceptable carrier once per day to the site of the partial thickness wound, thereby accelerating re-epithelialization of the partial thickness wound, wherein acceleration of re-epithelialization comprises one or more of the following:

the partial thickness wound is completely re-epithelialized by about day 6 after wounding, wherein the topical composition comprises at least 1% CoQ10 administered once a day for 5 days; or the time to achieve complete re-epithelialization of the partial thickness wound is reduced by about 3 days as compared to an untreated partial thickness wound, wherein the topical composition comprises at least 1% CoQ10 administered once a day for 5 days.

2. A method of accelerating proliferation and migration of fibroblasts and keratinocytes in a partial thickness wound, comprising administering a topical composition comprising a therapeutically effective amount of CoQ10 and liposomes, wherein the composition comprises between about 0.001% and about 60% (w/w) of CoQ10, and a pharmaceutically acceptable carrier once per day to the site of the partial thickness wound, thereby accelerating proliferation and migration of fibroblasts and keratinocytes in the partial thickness wound, wherein acceleration of proliferation and migration of fibroblasts and keratinocytes is determined by one or more of the following:

the partial thickness wound is completely re-epithelialized by about day 6 after wounding, wherein the topical composition comprises at least 1% CoQ10 administered once a day for 5 days; or the time to achieve complete re-epithelialization of the partial thickness wound is reduced by about 3 days as compared to an untreated partial thickness wound, wherein the topical composition comprises at least 1% CoQ10 administered once a day for 5 days.

3. The method of claim 1 or 2, wherein the composition increases ATP production and cell proliferation.

4. The method of claim 1 or 2, wherein the composition further mitigates pain from the wound.

5. The method of claim 1 or 2 wherein the composition is in the form of a gel, ointment, cream, salve, lotion, spray, aerosol, mousse, foam, liniment, or paste.

6. The method of claim 1 or 2, wherein the composition further comprises one or more of cytokines, growth factors, migratory factors, monokines, lymphokines, differentiation factors, hormones, analgesics, and pain-killers.

7. The method of claim 1 or 2, wherein the composition is administered through diffusion from a device impregnated with the composition.

8. The method of claim 1 or 2, wherein the topical composition further comprises one or more of Glycerol, Butylated hydroxytoluene, Ethanol, Medium Chain Triglycerides, and lavender.

9. The method of claim 1 or 2, wherein the topical composition further comprises one or more antimicrobial agents.

10. The method of claim 9, wherein the one or more antimicrobial agents comprises phenylmercuric nitrate or acetate, benzalkonium chloride, chlorhexidine acetate, or a combination thereof.

11. The method of claim 1 or 2, wherein the topical composition further comprises a surface active agent.

12. The method of claim 11, wherein the surface active agent comprises an anionic, cationic or non-ionic surface active sorbitan esters or polyoxyethylene derivatives thereof.

13. The method of claim 1 or 2, wherein the topical composition further comprises a suspending agent.

14. The method of claim 13, wherein the suspending agent comprises a natural gum, cellulose derivative, a silicaceous silicas, or a combination thereof.

15. The method of claim 1 or 2, wherein the topical composition further comprises one or more excipients selected from the group comprising lactose, sucrose, mannitol, or sorbitol, cellulose, maize starch, wheat starch, rice starch, potato starch, gelatin, gum tragacanth, methyl cellulose, hydroxypropylmethyl-cellulose, sodium carboxymethylcellulose, and polyvinyl pyrrolidone (PVP).

16. The method of claim 1 or 2, wherein the topical composition further comprises a buffer system.

17. The method of claim 1 or 2, wherein the topical composition further comprises water.

18. The method of claim 1 or 2, wherein the topical composition further comprises a transdermal skin penetration enhancer.

19. The method of claim 18, where the transdermal skin penetration enhancer comprises one or more of dimethylsulfoxide cyclic amide, N-methyl-2-pyrrolidone, 2-pyrrolidone, 2-pyrrolidone-5-carboxylic acid, N-(2-hydroxyethyl)-2-pyrrolidone, 1-lauryl-4-methoxycarbonyl-2-pyrrolidone, N-tallowalkylpyrrolidone, polyol, linear and branched fatty acid, alcohol, anionic surfactant, cationic surfactant, nonionic surfactant, ethoxylated fatty acid, ethoxylated alcohol, terpene, eucalyptus oil, polyoxyethylene sorbitan monopalmitate, polyoxyethylene sorbitan monostearate, polyoxyethylenesorbitan monooleate, sorbitane monostearate and-methyl salicylate.

20. The method of claim 19, wherein the transdermal skin penetration enhancer comprises Polyoxyethylene sorbitan monopalmitate, Polyoxyethylene sorbitan monooleate, or Sorbitane monostearate.

21. The method of claim 19, wherein the alcohol comprises ethanol, propanol, butanol, octanol, oleyl, stearyl, or linoleyl.

22. The method of claim 1 or 2, wherein the topical composition further comprises a solvent, a buffer, a penetration enhancer, and a viscosity modifier.

23. The method of claim 22, wherein the solvent comprises glycerol or propylene glycol.

24. The method of claim 13, wherein the suspending agent comprises silicaceous silicas.

25. The method of claim 1 or 2, wherein the topical composition further comprises an excipient sugar.

26. The method of claim 18, where the transdermal skin penetration enhancer comprises one or more of N,N-dimethyl acetamide (DMA) N,N-diethyl toluamide, N,N-dimethyl formamide, N,N-dimethyl octamide, N,N-dimethyl decamide, salicyclic acid, citric acid, and succinic acid.

27. The method of claim 2, wherein the composition accelerates re-epithelialization of the partial thickness wound, thereby accelerating healing of the partial thickness wound.

28. The method of claim 1, wherein the CoQ10 is encapsulated in liposomes.

29. The method of claim 2, wherein the CoQ10 is encapsulated in liposomes.

30. The method of claim 1 or 2, wherein the partial thickness wound does not require formation of granulation tissue for healing.

31. The method of claim 1 or 2, wherein the partial thickness wound is not greater than 0.5 mm in depth.

* * * * *